(12) United States Patent
Smith et al.

(10) Patent No.: US 11,300,483 B2
(45) Date of Patent: Apr. 12, 2022

(54) VERSATILE PASSIVE AIR SAMPLER

(71) Applicant: SKC, Inc., Eighty Four, PA (US)

(72) Inventors: Donald Lee Smith, Finleyville, PA (US); Linda Coyne, Pittsburgh, PA (US)

(73) Assignee: SKC, INC., Eighty Four, PA (US)

( * ) Notice: Subject to any disclaimer, the term of this patent is extended or adjusted under 35 U.S.C. 154(b) by 0 days.

(21) Appl. No.: 16/914,626

(22) Filed: Jun. 29, 2020

(65) Prior Publication Data

US 2020/0393341 A1 Dec. 17, 2020

Related U.S. Application Data

(63) Continuation of application No. 15/051,793, filed on Feb. 24, 2016, now Pat. No. 10,697,864.

(60) Provisional application No. 62/119,900, filed on Feb. 24, 2015.

(51) Int. Cl.
*G01N 1/22* (2006.01)
*G01N 33/00* (2006.01)

(52) U.S. Cl.
CPC ......... *G01N 1/2214* (2013.01); *G01N 1/2205* (2013.01); *G01N 1/2226* (2013.01); *G01N 1/2247* (2013.01); *G01N 1/2273* (2013.01); *G01N 33/0004* (2013.01); *G01N 33/0009* (2013.01); *G01N 33/0031* (2013.01); *G01N 33/0036* (2013.01); *G01N 33/0075* (2013.01)

(58) Field of Classification Search
CPC ............ G01N 1/2214; G01N 33/0009; G01N 1/2205; G01N 33/0004; G01N 33/0075; G01N 33/0031; G01N 1/2247; G01N 1/2226; G01N 33/0036; G01N 1/2273
See application file for complete search history.

(56) References Cited

U.S. PATENT DOCUMENTS

| | | |
|---|---|---|
| 5,517,866 A | 5/1996 | Manning et al. |
| 5,651,810 A * | 7/1997 | Flaherty ............. B01D 46/0091 95/287 |
| 5,717,147 A | 2/1998 | Basch et al. |
| 7,073,402 B2 | 7/2006 | Trakumas et al. |
| 7,980,147 B2 | 7/2011 | Tang |
| 8,082,808 B2 * | 12/2011 | Freeman ............... G01N 1/2273 73/863.21 |
| 2005/0279182 A1 | 12/2005 | Cole et al. |
| 2007/0163436 A1 | 7/2007 | Guild |
| 2012/0216597 A1 | 8/2012 | Park et al. |
| 2013/0031955 A1 | 2/2013 | Zimbron et al. |
| 2016/0209298 A1 | 7/2016 | O'Connell et al. |

* cited by examiner

*Primary Examiner* — David L Singer
*Assistant Examiner* — Anthony W Megna Fuentes
(74) *Attorney, Agent, or Firm* — The Webb Law Firm

(57) ABSTRACT

A passive air sampler is designed to allow for multiple sorbents and multiple sampling rates. The passive air sampler is also reusable and has interchangeable sorbents.

20 Claims, 8 Drawing Sheets

VERSATILE PASSIVE AIR SAMPLER

CROSS-REFERENCE TO RELATED APPLICATIONS

This Application is a Continuation Application of U.S. application Ser. No. 15/051,793, filed on Feb. 24, 2016, and entitled Versatile Passive Air Sampler, which claims the benefit of U.S. Provisional Application No. 62/119,900, filed on Feb. 24, 2015, and entitled Versatile Passive Air Sampler, the contents of which are hereby incorporated by reference in their entirety.

STATE REGARDING FEDERALLY SPONSORED RESEARCH OR DEVELOPMENT

Not applicable

THE NAMES OF THE PARTIES TO A JOINT RESEARCH AGREEMENT

Not applicable

BACKGROUND OF THE INVENTION

Field of the Invention

The invention relates to air sampling and particularly to sampling badges to be worn by individuals or placed in areas having possible air contaminants.

Description of the Related Art

Various types of badges have been designed for workers to wear to monitor and sample contaminants in the air. Badges are also suspended or placed in indoor and ambient air settings, independent of personnel. Many such badges are made to sample a single constituent even though there may be more than one possible contaminant in the atmosphere inhaled by the worker. Some badges in the past have also been limited to a certain absorbent or adherent for collecting the contaminant, such as charcoal, sorbent media, or treated paper. Uptake rates (sampling rates) have also been limited simply because of the construction of the badge.

There is a need for more versatility in badge air sampling design.

BRIEF SUMMARY OF THE INVENTION

At least two different collection media or compositions can be accommodated in our invention, and different sampling rates—that is, different uptake rates—can be prescribed for each medium.

As is known in the art of air sampling, the "uptake rate" of a diffusion sampler is directly proportional to the diffusion coefficient of the collected contaminant and the area of the diffusion barrier, and inversely proportional to the thickness of the barrier. An important characteristic of the barrier is the number and size of holes in it—a high sampling rate sampler may have a high number of holes in the barrier.

Our sampler may be constructed in the form of a badge having a nonsampling side, at least two sampling sides and a clip for attaching it to the user's clothing or to a device in an indoor environment or outdoor setting. As normally worn, the nonsampling side is closest to the wearer, and the at least two sampling sides are exposed to the atmosphere immediately in front of the wearer. The device includes a frame defining the sides and also defining chambers for at least two sampling units comprising collection media.

By a sampling unit (we may also call it an air contaminant collecting unit), we mean a permeable pouch containing a predetermined amount of sorbent, charcoal or other material, or a portion of treated paper, known to absorb a contaminant. Such sampling units will be described further below.

Each chamber defined by the frame may comprise an impermeable back preferably conforming in shape to a side of a sampling unit, and includes an open front which is covered by a removable barrier that is air-permeable or contains a desired number and size of holes or other means to provide access for the air to pass into the chamber and the sampling unit within it.

Prior to use, the entire body of the badge, or at least the sampling sides, is or are covered, preferably hermetically, by a sleeve, which may be rigid or not, to prevent contamination before use. The sleeve can be replaced after each use to prevent further intake of contaminants after the prescribed or desired time of exposure.

BRIEF DESCRIPTION OF THE SEVERAL VIEW OF THE DRAWING

Figure 5:
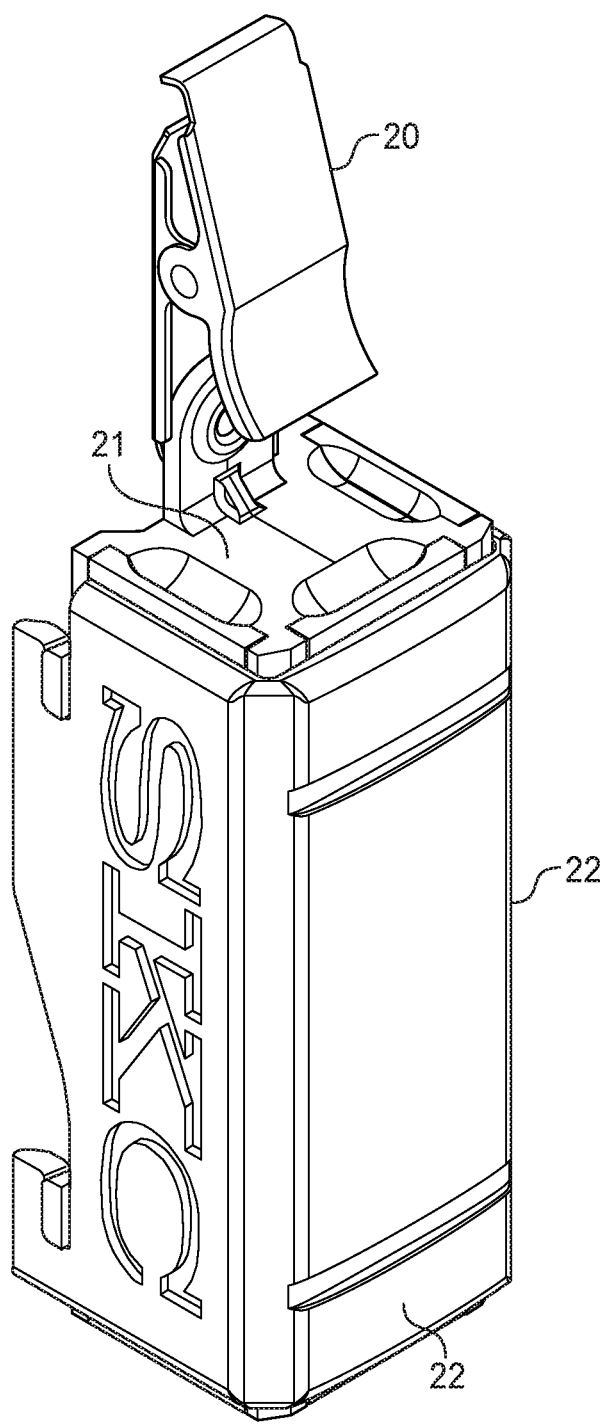
FIG. 5 is a perspective view of our sampler having three sampling sides.
Figure 7:
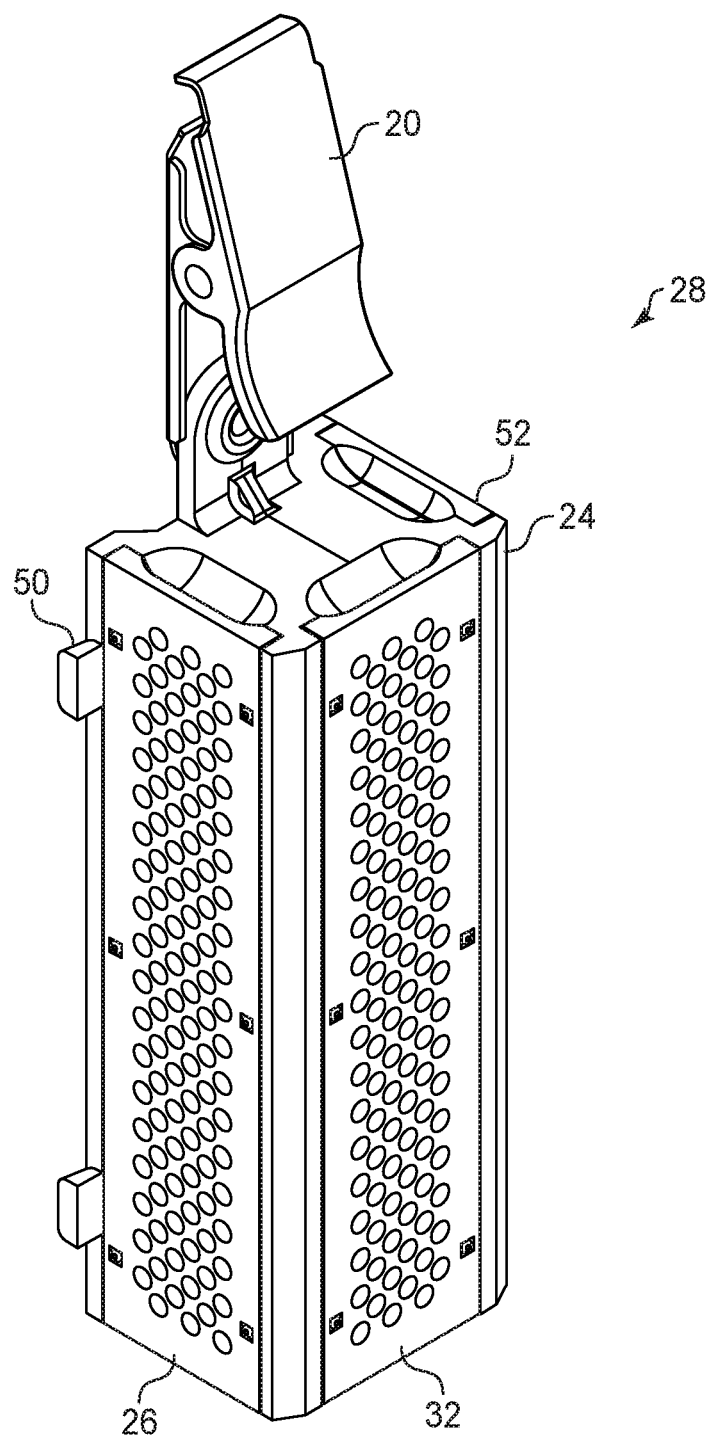

In FIG. 7, sampling is complete and the device of FIG. 5 is ready for sealing with the sleeve.

Figure 8:
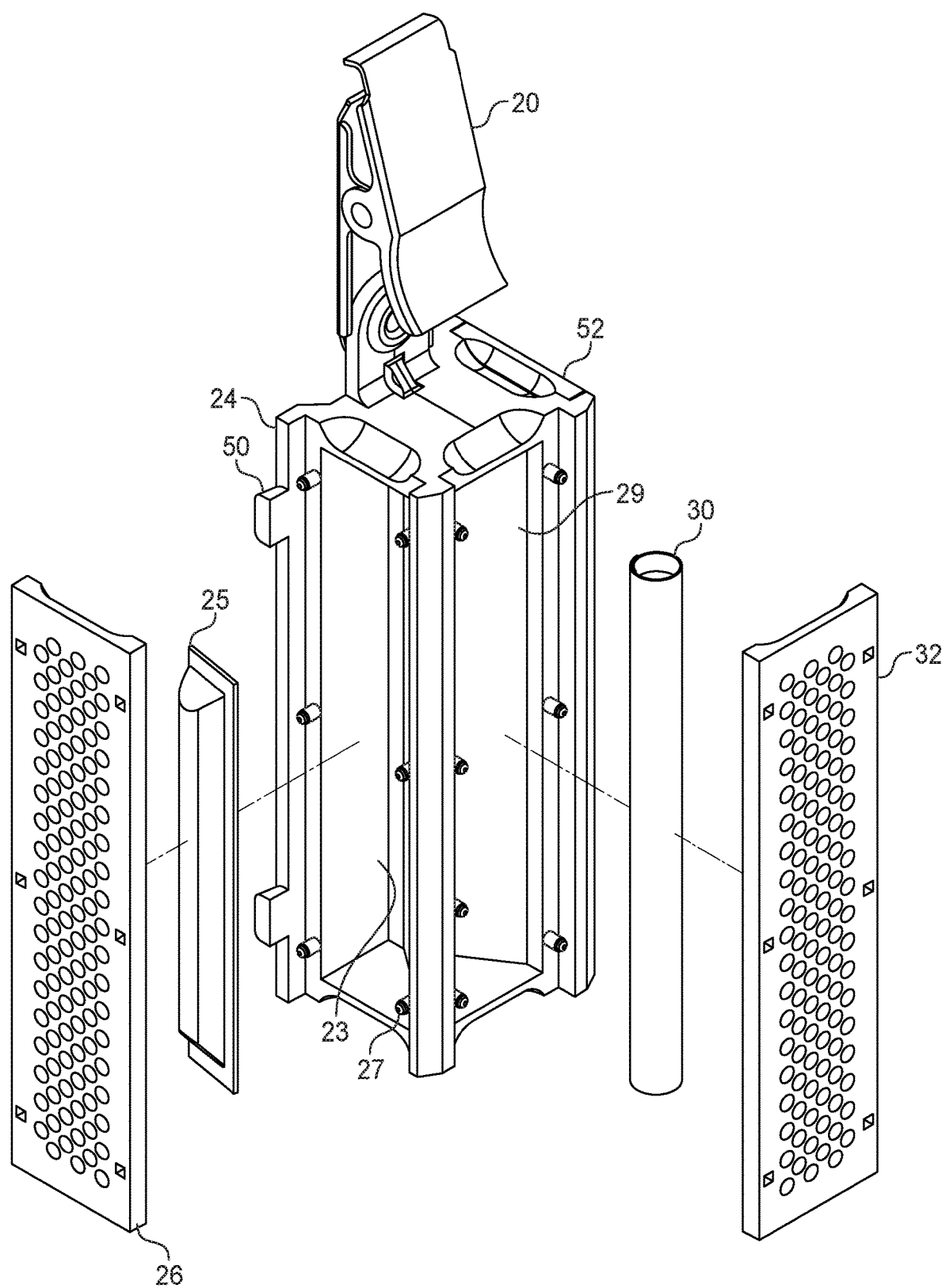

FIG. 8 is an exploded view of the device of FIG. 5.

DETAILED DESCRIPTION OF THE INVENTION

The invention will be described with respect to the two-element sampler of FIG. 1 and the three-element sampler of FIG. 5. It should be understood, however, that the concepts of the invention are applicable also to even more versatile devices. In particular, it will be seen that in both FIG. 1 and FIG. 5, the sampler takes the form of a badge which can be worn on a person's clothing or attached by its clip to a fixed or moving piece of furniture, equipment, or even hung from a branch of a tree. Where the sampler is not to be worn on a person's clothing, however, the clip is not necessary; it can be suspended on a wire or string or simply placed on a fixture or piece of furniture. The sampler is not illustrated without the clip, but the clip is not necessary in some forms of the invention.

Figure 1:
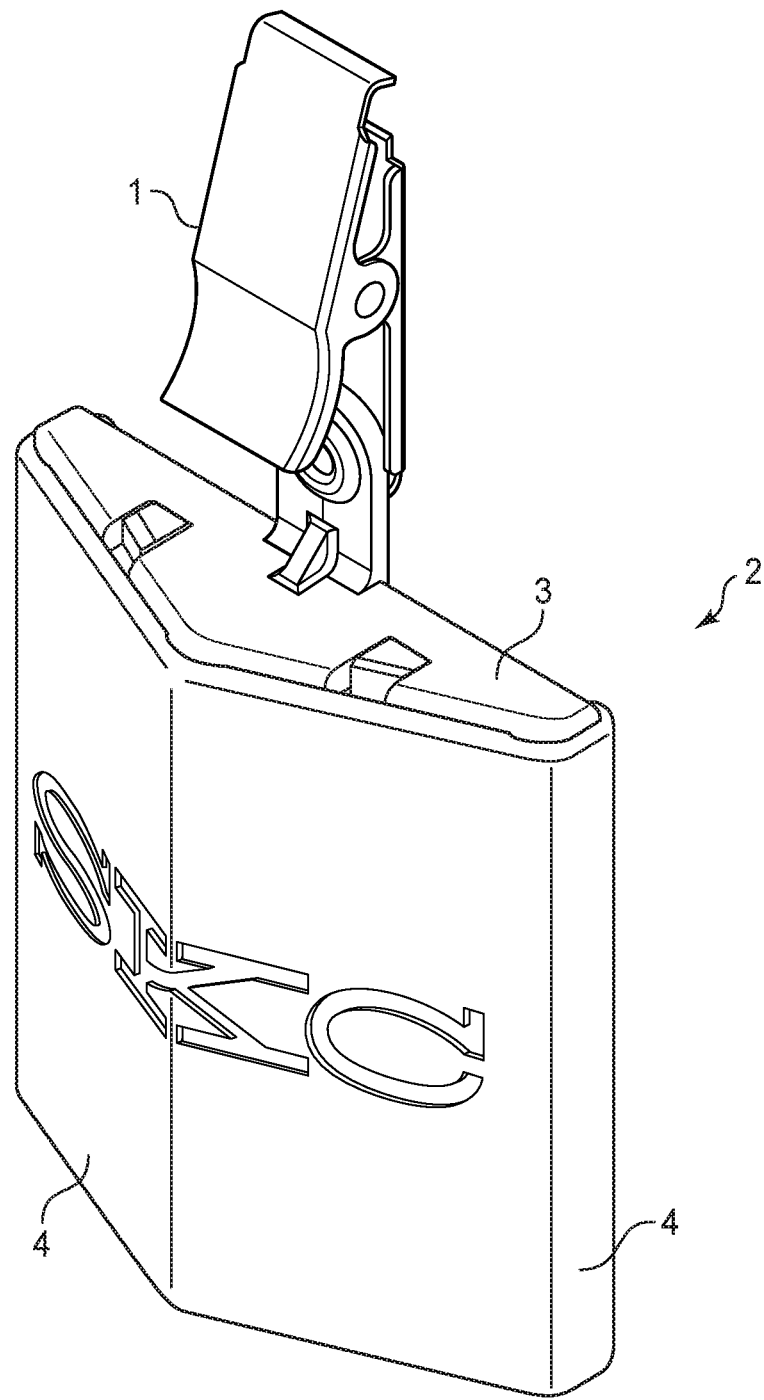
FIG. 1 is a perspective view of a two-element sampler.

Referring now to the perspective view of FIG. 1, it will be seen that the device in the form of a badge, as sold, or as received by the customer, comprises a spring-actuated clip 1 connected to a badge body 2. In this view, the badge body 2 comprises a substantially triangular body top 3 and a sleeve 4. The internal features will be described with respect to FIGS. 2-4. It should be observed here, however, that our invention is not limited to the angles shown for the substantially triangular shape. That is, while FIGS. 1-4 illustrate a generally flat triangular shape, the shape could be even flatter, rectangular, indented, or a far more acute isosceles triangular shape.

Figure 2:
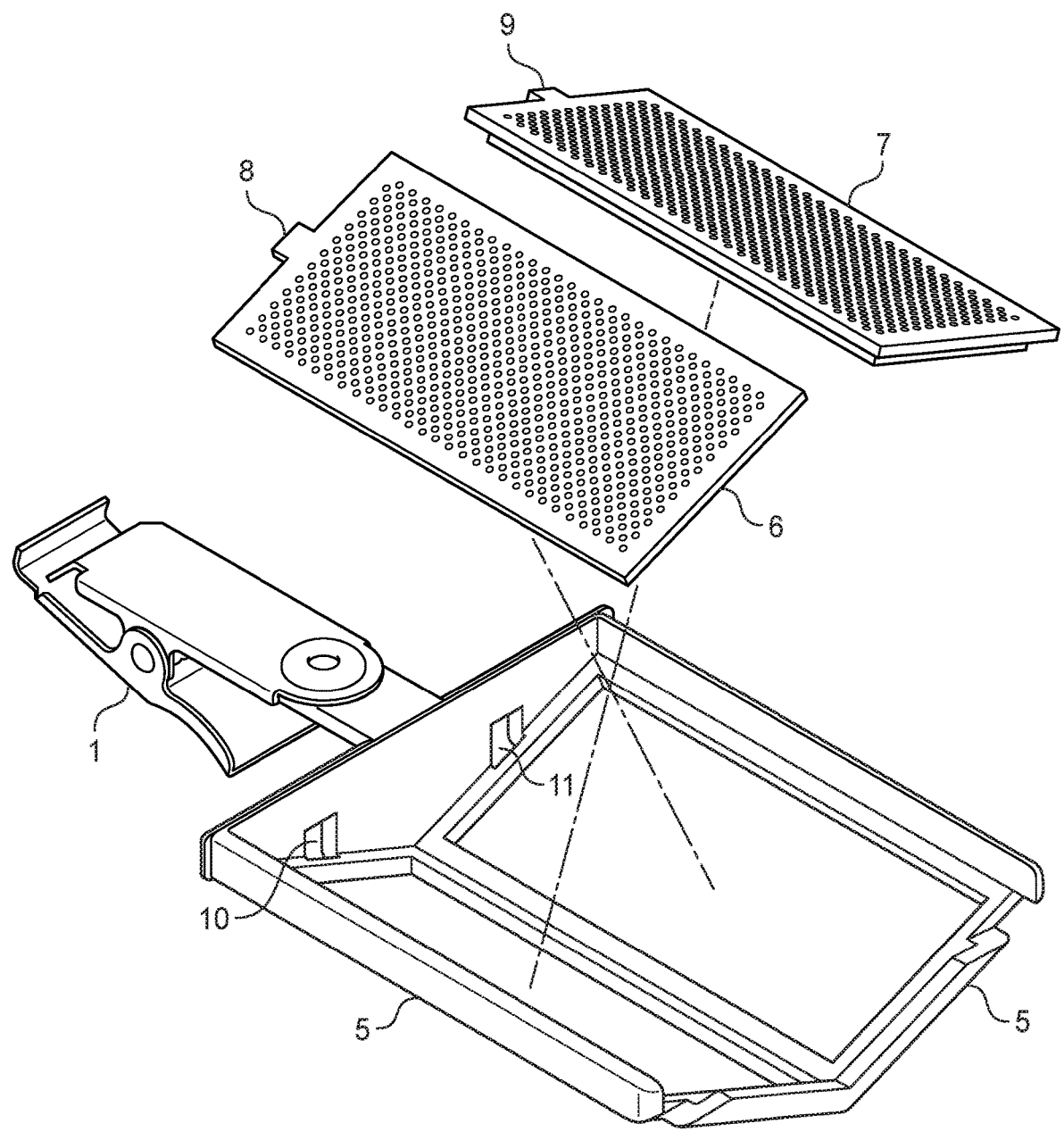
FIG. 2 shows a dissembled sampler of FIG. 1 prior to insertion of the sampling units.

FIG. 2 is a rear view of the dissembled badge, showing clip 1 and the body frame 5 which defines the shape of the body 2 (FIG. 1). Badge barriers 6 and 7 are shown ready to be inserted in place in frame 5 as a beginning step in assembling the badge for use. Barriers 6 and 7 are permeable or contain holes (not shown) to permit air to pass through them. Barriers 6 and 7 have tabs 8 and 9 adapted for insertion into sockets 10 and 11 in body top 3. On inserting tabs 8 and 9 into sockets 10 and 11, the barriers 6 and 7 are snapped into place in body frame 5, thus forming the outer surfaces of the badge to be exposed to the ambient atmosphere. Barriers 6 and 7 may be made of different materials and may contain different numbers of holes, allowing for different permeability and for many different uptake rates, depending on the types of samples to be collected and the desired rates of sampling.

Figure 3:
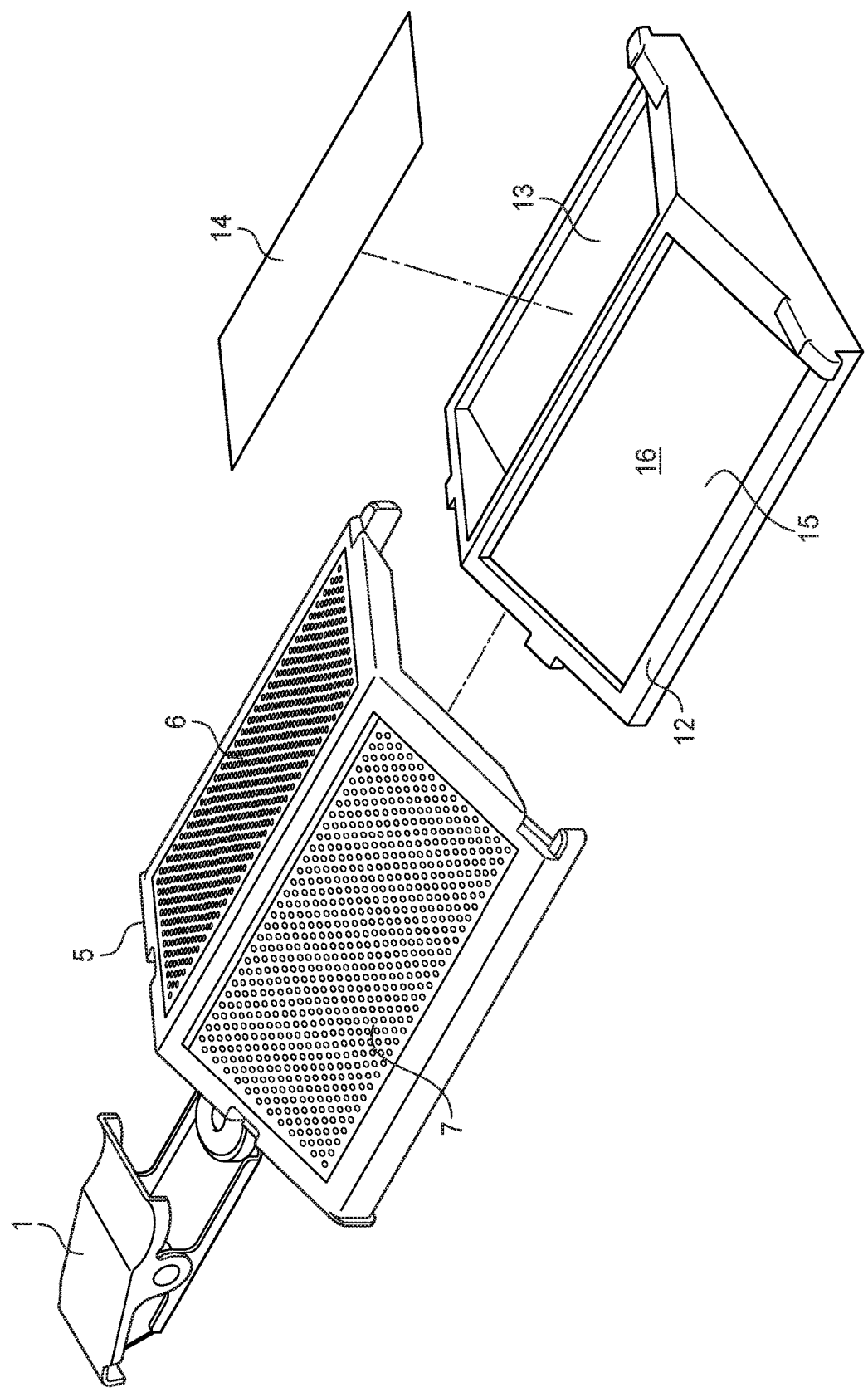
FIG. 3 illustrates insertion of sorbent pouches (media sample container) into the device of FIG. 1.

The next step in assembling the badge sampler is shown in FIG. 3. Unlike FIG. 2, body frame 5, now containing barriers 6 and 7, is shown from the front. Body frame 5 is positioned to receive insert 12, which contains sampling chamber 13, illustrated as ready to receive treated paper 14, and sampling chamber 15, already occupied by pouch 16 containing a sorbent. Insert 12 is designed to slide snugly into body frame 5. Insert 12 has a back panel, not shown. The back panel is impermeable, covers the entire back side of insert 12, and will normally be in loose contact with the user's clothing as the badge hangs from it. It should be noted, however, that where the sampler is not designed to be worn by a person, but rather to be placed or suspended openly either indoors or outdoors, the impermeable back panel is not necessary, and the sampler may contain a third, fourth, or other chamber, each covered with an appropriate barrier, for varied contaminant collection. Pouch 16 is made of mesh or other permeable material designed to admit the type of air contaminant to be collected; pouch 16 contains a sorbent normally also selected specifically to absorb a contaminant to be sampled. Chamber 13 could also accommodate a pouch, but is shown as ready to receive treated paper 14, which is selected to pick up a desired component of the air. Any other type of medium for absorbing, adhering, or otherwise picking up a target contaminant may be placed in the chamber. An inert spacer, not shown, may be used to place the treated paper 14 in a desired orientation in chamber 13. After both chambers 13 and 15 are filled with the desired sorbent, paper, or other sampling device or material, insert 12 is inserted into the conforming shape of body frame 5 and snapped into place.

After assembling as shown in FIGS. 2 and 3, the badge is ready for use. The user should be aware of and follow the protocols for sampling, such as placement of the badge on the clothing, timing the exposure while wearing the badge, and terminating the sampling session.

Figure 4:
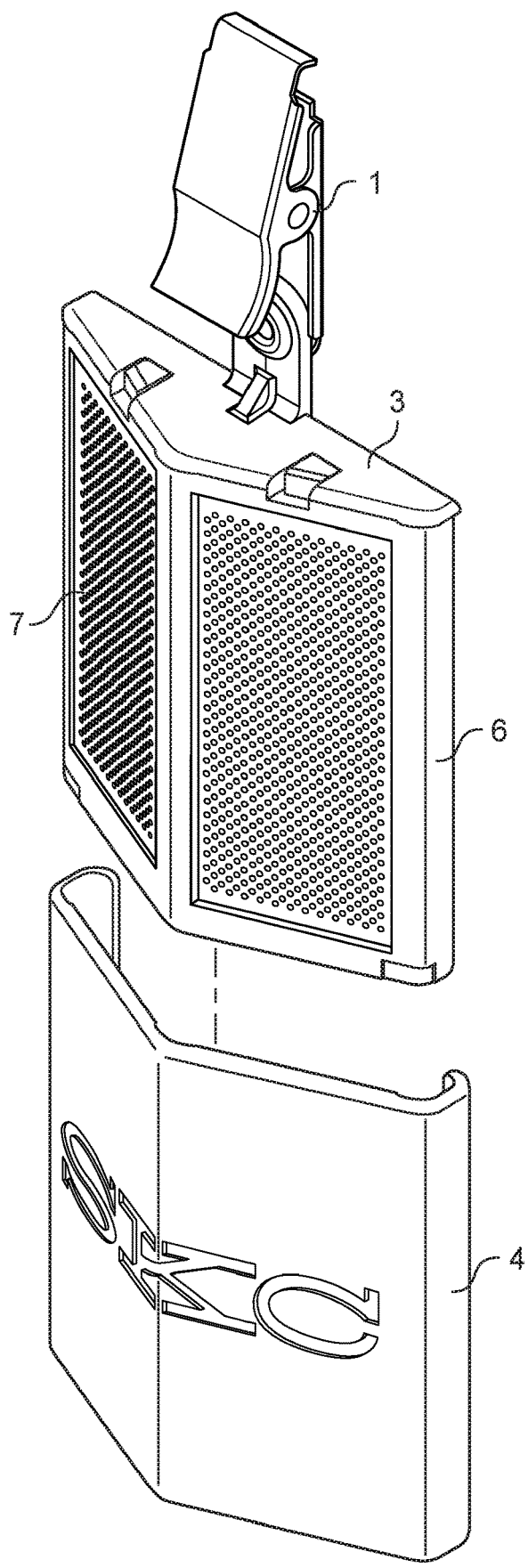
FIG. 4 shows fixing the sleeve of the FIG. 1 device for shipment or storage prior to use.

When the wearer's shift or other timed period is complete, accurate results require that sleeve 4 be placed over the barriers 6 and 7, as shown in FIG. 4. Sleeve 4 conforms to the shape of the badge and forms a seal when the badge is slid into it as illustrated.

Referring now to FIG. 5, a variant of the invention is shown capable of taking three different air samples. The perspective view of FIG. 5 is the complete sampler before use (it need not contain any sorbent or other collector) or after use (in a sealed state to preserve the integrity of the samples). This view shows clip 20 for attaching to the user's clothing, similar to clip 1 in FIGS. 1-4, a body top 21, and a sleeve 22 sealing the three sampling sides not visible behind the sleeve 22. Clip 20 is connected to a back side not visible in this view. As indicated elsewhere herein, a clip may not be necessary if the sampler is to be used for area sampling rather than personnel wear, although the clip may facilitate positioning of the sampler in an open space where there is something for it to clip to. We do not intend to be limited to the generally square cross section of the device as shown—a four sided badge may be substantially trapezoidal in cross section, for example, wherein the back side is a relatively long base, the two sides are at acute angles from the base, and the front and sides meet at obtuse angles. The overall shape of the badge may be slightly tapered as shown to facilitate fitting the sleeve 22 over the body (concealed by the sleeve 22 in this view). The shape could be other shapes such as an oval.

Figure 6:
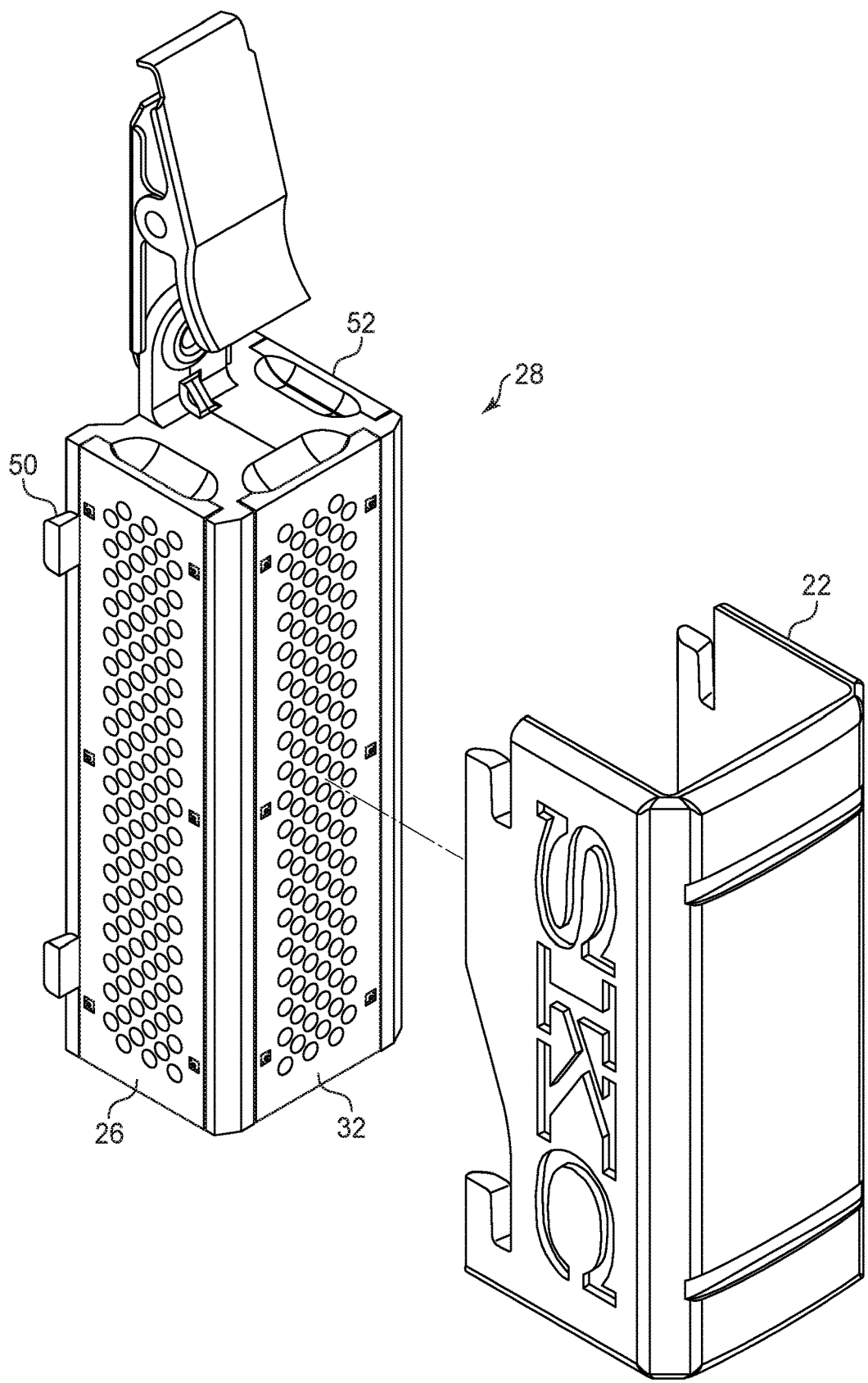
FIG. 6 shows one of the chambers of the device of FIG. 5; the sorbent pouch (media sample container) and barrier are ready for assembly.

In FIG. 6, sleeve 22 has been removed to show chamber 23 on the front side of body 24. Chamber 23 (shown in FIG. 8) is empty but pouch 25 (shown in FIG. 8) is poised for placement into it. Pouch 25 contains sorbent or other material for collection of a desired specimen from the air. Pouch 25 is similar to pouch 16 in FIG. 3, for example, in that it is made of mesh or other permeable material that permits the passage of air and the target contaminant. The shape of pouch 25 substantially conforms to the shape of chamber 23, however the pouch could be a different shape. Also poised for assembly is barrier 26, which will cover pouch 25 after snapping into place using pegs 27 on body 24 and corresponding holes not shown on barrier 26. Barrier 26 is similar to barriers 6 and 7 in FIGS. 1-4 in that it is made of material that is permeable to air and/or includes holes appropriate for permitting the flow of air into chamber 23 and pouch 25. Barrier 26 can have different holes sizes and shapes. Also shown is barrier 52 and peg 50. Peg 50 allows for the sleeve 22 to slideably attach and lock onto body 24 (shown in FIG. 7). If multiple barriers are used each barrier can have its own sampling rate based on the different hole sizes, numbers or shapes.

Chambers on the two sides of the badge may be filled, and barriers placed, in the same way as will be shown more clearly with respect to FIG. 8.

In FIG. 7, the fully assembled, unenclosed sampler 28 is shown as it appears during use. When the sampling session is over, the unenclosed sampler 28 is inserted and sealed into sleeve 22 until it is analyzed in an appropriate laboratory setting, where the sleeve 22 will be removed and the pouches handled according to protocol.

The exploded view of FIG. 8 illustrates that the device of FIGS. 5-7 includes a chamber 23 and a similar chamber on its opposite side. For chambers 23, 29 and the third chamber opposite chamber 23 a pouch (25, 30) is shown, and barriers 26, 32, and 52 are poised for placement as described with respect to FIG. 6. The assembled unit ready for use will appear as item 28 in FIG. 7.

Our device is reusable. It is highly versatile in that many different types of sorbents, extractants, and adhering surfaces can be employed, while at the same time the uptake rate of the barriers can be changed and varied almost infinitely. Barriers in a range of very high and very low permeability can be employed while the chambers can contain the same or different materials, pouches, papers, types of charcoal, or the like. All of this variability can take form in different numbers of chambers. This provides for a very large possible combination of capabilities for the sampler.

Some of the sorbent and other materials that can be in the containers include activated carbon, activated charcoal, graphitized carbons, carbon molecular sieves, silica gel, XAD resins (including but not limited to XAD-2 resin), CHROMOSORB resins, TENAX TA, ANASORB 747 beaded carbon, treated carbons and charcoals, treated silica, treated ANASORB 747, treated XAD resins (including but not limited to XAD-2 resin), gels, treated charcoal and any other material known to absorb or adsorb an air contaminant such as porous polymers.

CHROMOSORB is a registered trademark currently owned by IMERYS MINERALS CALIFORNIA, INC. CORPORATION DELAWARE 1732 NORTH FIRST STREET, SUITE 450 SAN JOSE CALIFORNIA 95112, it can be purchased from Advanced Minerals Corporation. In general it is a sorbent. More specifically it can be diatomite and polymer based sorbents.

XAD is a registered trademark currently owned by ROHM AND HASS COMPANY, a Delaware corporation, 1732 North First Street, Suite 450 San Jose Calif., 95112. In general they are polymeric and carbonaceous sorbents.

TENAX TA is a registered trademark currently owned by BUCHEM B.V. CORPORATION NETHERLANDS Minden 60 7327 AW Apeldoorn NETHERLANDS. In general TENAX is a sorbent. Specifically, it can be a porous polymer based on 2,6-diphenyl-p-phenyleneoxide.

ANASORB is a registered trademark of SKC, Inc. CORPORATION PENNSYLVANIA 863 Valley View Road Eighty Four PENNSYLVANIA 15330 and can be purchased directly from SKC. ANASORB is generally used in connection with sorbents used with air samplers. ANASORB 747 is typically a synthetic carbon with low ash content sorbent.

Types of mesh suitable for the pouches are stainless steel, nylon, Teflon mesh, or any other mesh suitable for the sorbent.

Typical permeability of the barrier could be from 0.5 to 130 milliliters per minute. Other rates are also possible.

The barrier can have any number of holes. Preferably the barrier will have between 1-1000 holes. Most preferably a barrier will have 5 holes to 111 holes per barrier (diffuser plate). On a three sided sampler with the most preferred barriers (5-111 holes), one of skill in the art will recognize the never seen before benefit of having the ability to alter sampling rate of the sampler. Under this scenario the sampler can have between 15 to 333 holes per badge. Differing amount of holes can also be used to obtain different rates.

Various changes could be made in the above construction and method without departing from the scope of the invention as defined in the claims below. It is intended that all matter contained in the above description, as shown in the accompanying drawings, shall be interpreted as illustrative and not as a limitation.

The invention claimed is:

1. A passive air sampler, comprising:
   (a) a frame defining at least two chambers so that each chamber has separate access to the same sampling environment and one chamber is sealed from the other chamber,
   (b) at least two air contaminant collecting units configured for placement in said at least two chambers,
   (c) wherein the frame comprises one or more pegs; and at least two air-permeable barriers, wherein each of the at least two air permeable barriers comprises a hole configured to be inserted into a respective peg of the one or more pegs of the frame, wherein the at least two air-permeable barriers are configured to cover said at least two chambers, and
   (d) a removable sleeve for sealing all of said at least two chambers when said passive air sampler is not in use, wherein each of said at least two air-permeable barriers is removably attached to its own respective chamber and interchangeable to change the air flow into and out of each chamber.

2. The passive air sampler of claim 1, wherein each of the at least two air-permeable barriers has between 1 and 1000 holes.

3. The passive air sampler of claim 2, including a third chamber, a third air contaminant collecting unit configured for placement in the third chamber, and a third air-permeable barrier.

4. The passive air sampler of claim 3, wherein one of the at least two air-permeable barriers has between 5 and 111 holes.

5. The passive air sampler of claim 1, including a first sorbent placed into one of the at least two air contaminant collecting units.

6. The passive air sampler of claim 5, including a second sorbent placed into another of the at least two air contaminant collecting units without the first sorbent, wherein the second sorbent is different from the first sorbent.

7. A method of obtaining samples of at least two air contaminants comprising (i) removing the sleeve from the passive air sampler of claim 1, (ii) exposing the passive air sampler to the air to be sampled for a desired period of time, and (iii) replacing the sleeve on said passive air sampler.

8. The method of claim 7, further including removing said removable sleeve and quantitatively determining a contaminant content of said at least two contaminant collecting units from said passive air sampler.

9. The passive air sampler of claim 1, including a clip configured to attach said passive air sampler to clothing.

10. The passive air sampler of claim 9, wherein said frame includes a side having an impermeable cover.

11. The passive air sampler of claim 1, wherein said at least two air-permeable barriers are removably attached to said frame.

12. The passive air sampler of claim 1, wherein the air contaminant sampling rate is regulated by the material of said at least two air contaminant collecting units and dimensions and number of holes in said at least two air-permeable barriers.

13. The passive air sampler of claim 1, wherein said frame defines three chambers.

14. The passive air sampler of claim 1, wherein said at least two air contaminant collecting units each comprise a material independently selected from the group consisting of activated charcoal, activated carbon, silica gel, co-polymers of styrene and divinylbenzene, graphitized carbon, diatomaceous-based resins, polymers based on 2,6-diphenyl-p-phenyloxide, synthetic carbon, treated silica gels, treated activated carbon, and treated charcoal.

15. The passive air sampler of claim 1, wherein at least one of said at least two air contaminant collecting units is in the form of a sample media container.

16. The passive air sampler of claim 15, wherein said sample media container is made of stainless steel, nylon, or a mesh suitable for a sample media.

17. The passive air sampler as recited in claim 16, wherein the sample media is a sorbent.

18. The passive air sampler as recited in claim 17, wherein the sorbent comprises a material selected from the group consisting of activated charcoal, activated carbon, graphitized carbons, carbon molecular sieves, silica gel, co-polymers of styrene and divinylbenzene, polymers based on 2,6-diphenyl-p-phenyloxide, synthetic carbon, treated silica gels, treated activated carbon, diatomaceous-based resins and treated charcoal.

19. A method of monitoring contaminants present in air comprising wearing the passive air sampler of claim 18 as a badge without the removable sleeve for a desired period of time, and determining the contaminant content of one of the at least two contaminant collecting units.

20. The passive air sampler as recited claim 1, wherein at least one of said at least two air contaminant collecting units is in the form of a sorbent.

\* \* \* \* \*